(12) United States Patent
Olson et al.

(10) Patent No.: US 8,282,619 B2
(45) Date of Patent: Oct. 9, 2012

(54) GARMENT-LIKE ABSORBENT ARTICLE

(75) Inventors: Christopher Peter Olson, Neenah, WI (US); Lawrence Howell Sawyer, Neenah, WI (US); Raymond Gerard St. Louis, Fremont, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 71 days.

(21) Appl. No.: 12/835,369

(22) Filed: Jul. 13, 2010

(65) Prior Publication Data
US 2010/0292666 A1 Nov. 18, 2010

Related U.S. Application Data

(63) Continuation of application No. 10/105,043, filed on Mar. 22, 2002, now abandoned.

(51) Int. Cl.
*A61F 13/15* (2006.01)
(52) U.S. Cl. ............... 604/396; 604/385.3; 604/385.24; 604/385.29; 604/385.26
(58) Field of Classification Search .................. 604/396, 604/385.3, 385.24, 385.29, 385.26
See application file for complete search history.

(56) References Cited

U.S. PATENT DOCUMENTS

| 4,100,324 A | 7/1978 | Anderson et al. |
| 4,813,950 A | 3/1989 | Branch |
| 4,909,804 A | 3/1990 | Douglas, Sr. |
| 4,940,464 A | 7/1990 | Van Gompel et al. |
| 4,960,414 A | 10/1990 | Meyer |
| 5,098,419 A | 3/1992 | Gold |
| 6,168,585 B1 | 1/2001 | Cesco-Cancian |
| 7,411,110 B2 | 8/2008 | Sawyer et al. |

FOREIGN PATENT DOCUMENTS

| CA | 2 216 447 | 10/1996 |
| RU | 94027296 | 10/1996 |
| WO | WO 00/35401 A1 | 6/2000 |

*Primary Examiner* — Jacqueline F. Stephens
(74) *Attorney, Agent, or Firm* — Dority & Manning, P.A.

(57) ABSTRACT

A garment-like absorbent article includes an absorbent chassis that defines a waist opening and first and second leg openings. A longitudinal length of the chassis is optimized in a linear relationship with the waist circumference of the chassis, the circumference measured at 500 grams tension. With respect to the linear relationship, the thickness of the garment is substantially constant along the same line defined by the length and the circumference, and decreases as the y-intercept increases.

20 Claims, 12 Drawing Sheets

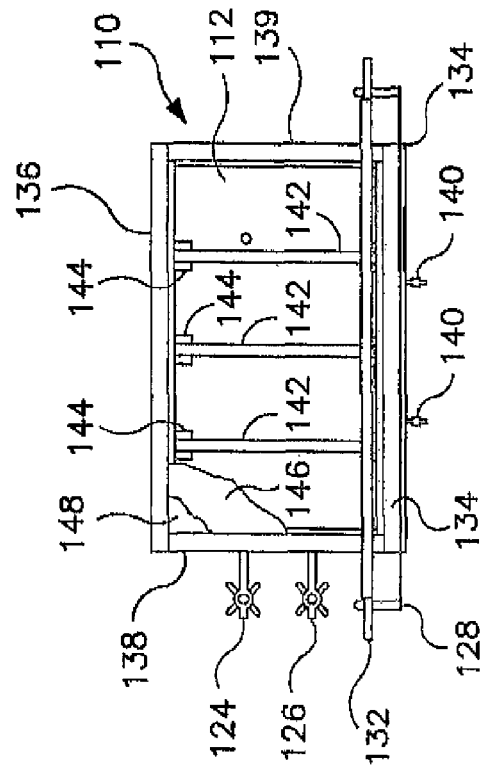
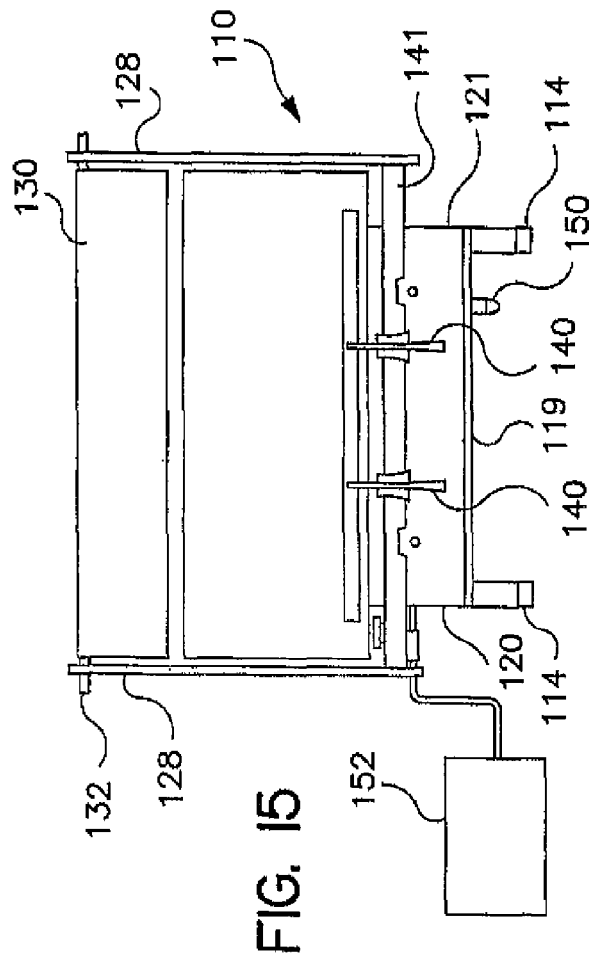
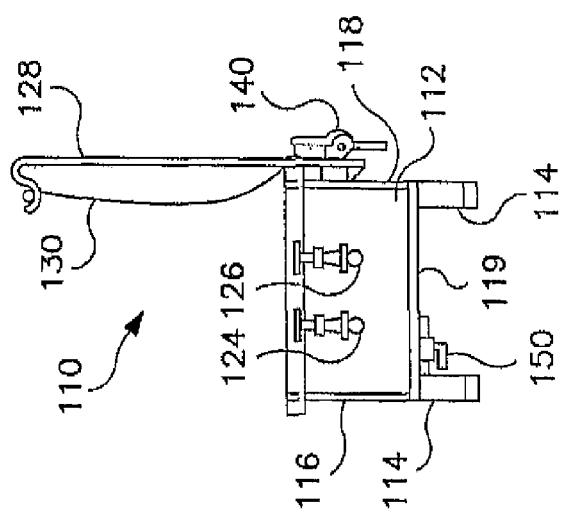

GARMENT-LIKE ABSORBENT ARTICLE

RELATED APPLICATIONS

The present application is a continuation application and claims priority to U.S. patent application Ser. No. 10/105,043 filed on Mar. 22, 2002 now abandoned.

BACKGROUND OF THE INVENTION

This invention is directed to a pant-like article that functions and feels like underwear, and also includes absorbent properties.

Pant-like absorbent garments, such as training pants, are designed as a transitional garment to assist a wearer in the transition from diapers to underwear during a toilet training process. Ideally, training pants should resemble underwear in terms of fit and comfort, while providing absorbent properties to catch any "accidents" that may occur while the wearer is wearing the garment. Unlike underwear, training pants can be bulky due to the volume of absorbent material contained therein. This bulkiness can make the garment feel more like a diaper than like underwear. Similarly, other types of pant-like absorbent garments, such as adult incontinence garments, swimwear, and diapers, include absorbent materials and, as a result, may seem bulky.

From a manufacturing point of view, it is desirable to include as little material as possible in each garment to generate cost savings in terms of material expenditures. From a consumer's point of view, it is desirable to include as much material as necessary to provide a comfortable fit as well as adequate absorbency and leak resistance. Thus, it is desirable to optimize the amount of material used in such garments by determining the least amount of material necessary to provide sufficient comfort and functionality.

Absorbent garments are typically constructed of multiple layers, with an absorbent layer positioned between an outer cover and a body side liner, for example. Additional layers, each having specialized functions, may also be included in the structure of absorbent garments, including, but not limited to, surge layers, spacer layers, and barrier layers. Each of these layers adds to the overall thickness of the garment, with the absorbent layer typically being the thickest layer of all. Generally, the thicker the garment, the longer the garment must be to envelop all of the intermediate layers, thus adding to the manufacturing cost of the garment.

There is thus a need or desire for an absorbent pant-like garment having optimized physical parameters, resulting in a garment that looks and feels like underwear. There is a further need or desire for an absorbent pant-like garment having an optimized length relative to the waist circumference of the garment with an optimized thickness, while maintaining a considerable level of flexibility and absorbent capacity.

SUMMARY OF THE INVENTION

In response to the discussed difficulties and problems encountered in the prior art, a new pant-like absorbent garment having optimized parameters has been discovered. The principles of the present invention may be applied to any of a number of personal care product applications, such as training pants, diapers, diaper pants, swimwear, adult incontinence products, and the like.

The pant-like absorbent garment of the invention includes an absorbent chassis that defines a waist opening and first and second leg openings. The longitudinal length of the garment is measured from a front waist edge of the chassis to a back waist edge of the chassis. The circumference of the waist opening is measured, for the purposes of the present invention, at 500 grams tension. In this invention, the length is optimized in a linear relationship with the waist circumference and the thickness of the garment. More particularly, the longitudinal length is proportional to the circumference of the waist opening according to the following linear relationship:

$$\text{Length} \leq (\text{Circumference} - b)/m,$$

where b is the y-intercept and m is the slope of the line. Even more particularly, it has been found that in the linear relationship of the garment of the invention, the slope (m) is 1.6 and the y-intercept (b) can be −99, or −114, or −128, depending on the maximum length or maximum thickness desired.

The thickness is substantially constant along the same line defined by the length and the circumference, and decreases as the y-intercept increases. Suitably, the thickness of the garment is less than about 4.5 millimeters, or less than about 4 mm, or less than about 3 mm, or less than about 2 mm. The length is between about 350 and about 650 millimeters, and the circumference is between about 450 and about 750 millimeters, Furthermore, the garment also has a considerable level of flexibility, and has an absorbent capacity of between about 100 and about 800 grams.

With the foregoing in mind, it is a feature and advantage of the invention to provide a pant-like absorbent garment having optimized parameters set forth in a linear relationship between the longitudinal length, waist circumference, and thickness of the garment.

BRIEF DESCRIPTION OF THE DRAWINGS

FIG. 13 representatively shows a partially cut away top view of a saturated capacity tester;

FIG. 14 representatively shows a side view of a saturated capacity tester; and

FIG. 15 representatively shows a rear view of a saturated capacity tester.

DEFINITIONS

Within the context of this specification, each term or phrase below will include the following meaning or meanings.

"Absorbent article" includes personal care garments, medical garments, and the like. The term "disposable garment" includes garments which are typically disposed of after 1-5 uses. The term "personal care garment" includes diapers, diaper pants, training pants, swim wear, absorbent underpants, adult incontinence products, feminine hygiene products, and the like.

"Attached" refers to the joining, adhering, connecting, bonding, or the like, of at least two elements. Two elements will be considered to be attached together when they are attached directly to one another or indirectly to one another, such as when each is directly attached to intermediate elements.

"Coform" refers to a material produced by combining separate polymer and additive streams into a single deposition stream in forming a nonwoven web. Such a process is taught, for example, by U.S. Pat. No. 4,100,324 to Anderson et al. which is hereby incorporated by reference.

"Layer" when used in the singular can have the dual meaning of a single element or a plurality of elements.

Figure 3:
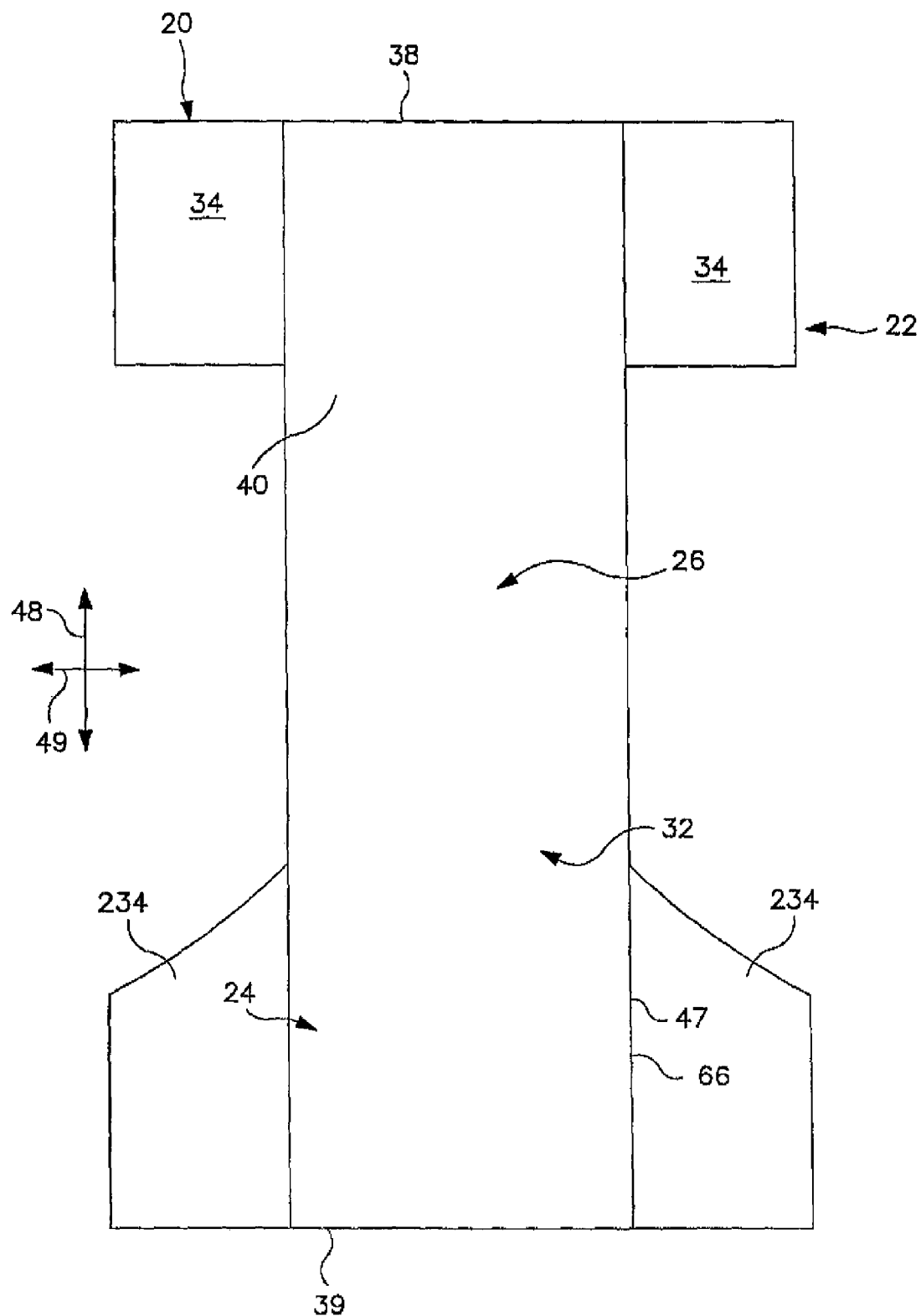
FIG. 3 is a plan view of the absorbent garment of FIG. 1 in a partially disassembled, stretched flat state, and showing the surface of the garment that faces away from the wearer when the garment is worn, according to one embodiment of this invention.
Figure 4:
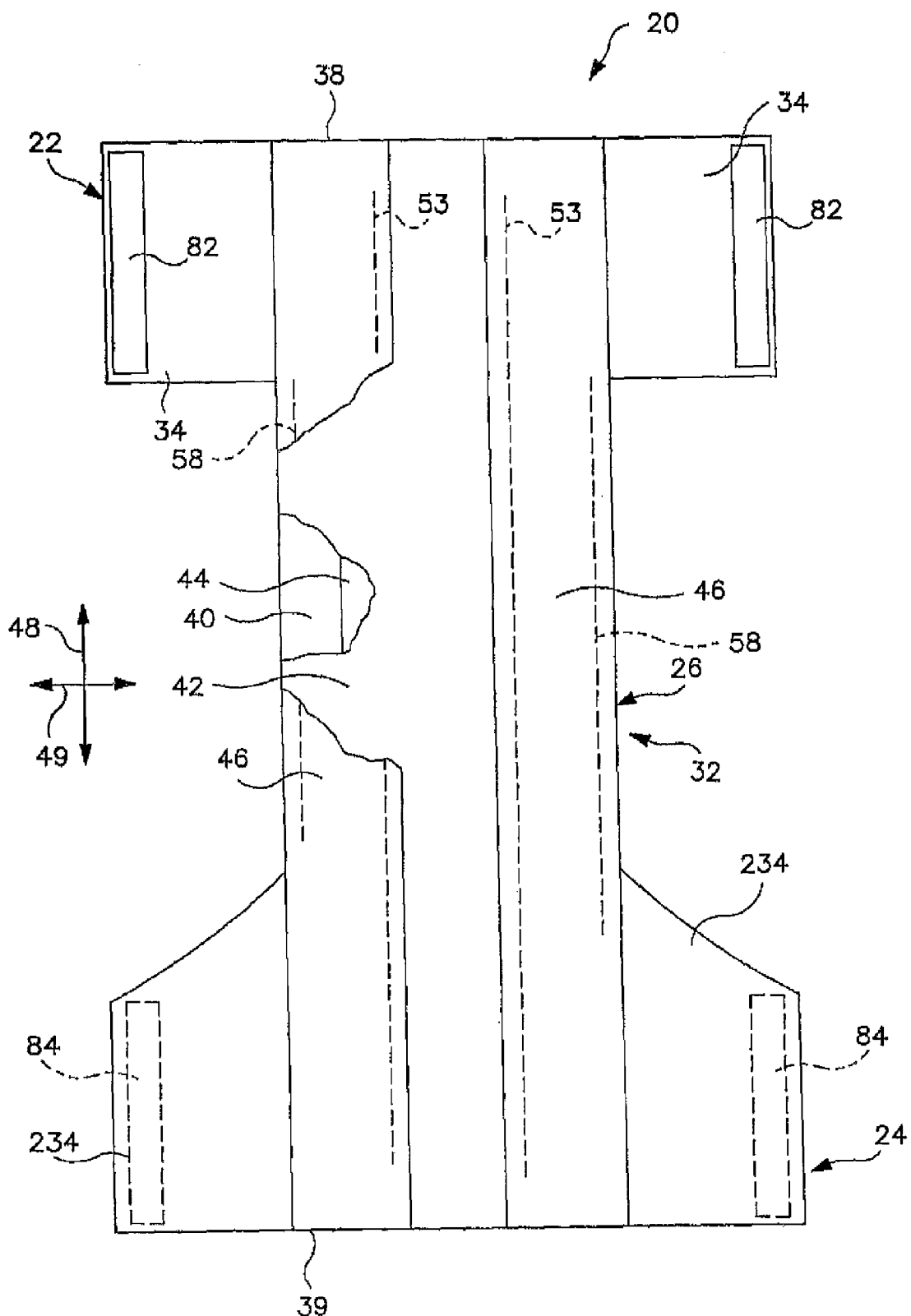
FIG. 4 is a plan view of the absorbent garment of FIG. 2 in a partially disassembled, stretched flat state, and showing the surface of the garment that faces the wearer when the article is worn, and with portions cut away to show the underlying features, according to one embodiment of this invention.

"Longitudinal" and "transverse" have their customary meaning, as indicated by the longitudinal and transverse axes depicted in FIGS. 3 and 4. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such processes are known in the art. Meltblown fibers are microfibers which may be continuous or discontinuous, are generally smaller than about 0.6 denier, and are generally self bonding when deposited onto a collecting surface.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced, as known in the art. Spunbond fibers are quenched and generally not tacky when they are deposited onto a collecting surface. Spunbond fibers are generally continuous and often have average deniers larger than about 0.3, more particularly, between about 0.6 and 10.

"Superabsorbent," "superabsorbent polymer," or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

These terms may be defined with additional language in the remaining portions of the specification.

DETAILED DESCRIPTION OF THE PRESENTLY PREFERRED EMBODIMENTS

The present invention is directed to a pant-like absorbent garment having optimized parameters. More particularly, a longitudinal length of the garment is proportional to a waist circumference of the garment according to a linear relationship. Furthermore, with respect to the length and circumference linear relationship, the thickness parameter of the garment is substantially constant along the same line defined by the length and circumference relationship, and decreases as the y-intercept increases.

The principles of the present invention can be incorporated into any suitable pant-like disposable absorbent article. Examples of such suitable articles include diapers, diaper pants, training pants, incontinence products, other personal care or health care garments, including medical garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

The term "training pant," as used herein, refers to a pant-style absorbent garment having either permanently bonded side seams or refastenable side seams that are packaged and sold in a pre-fastened, ready-to-wear position. In other words, the training pant is provided with a continuous waist circumference when the garment is delivered to the consumer with any pre-determined fastening determined by the manufacturer. Thus, the training pant has an automatic fit, as opposed to an adjustable fit, with a pertinent waist circumference determined by the manufacturer such that the training pant is packaged by the manufacturer in a user-friendly mode wherein a wearer can put the garment on without having to manually adjust any fastening devices.

Figure 1:
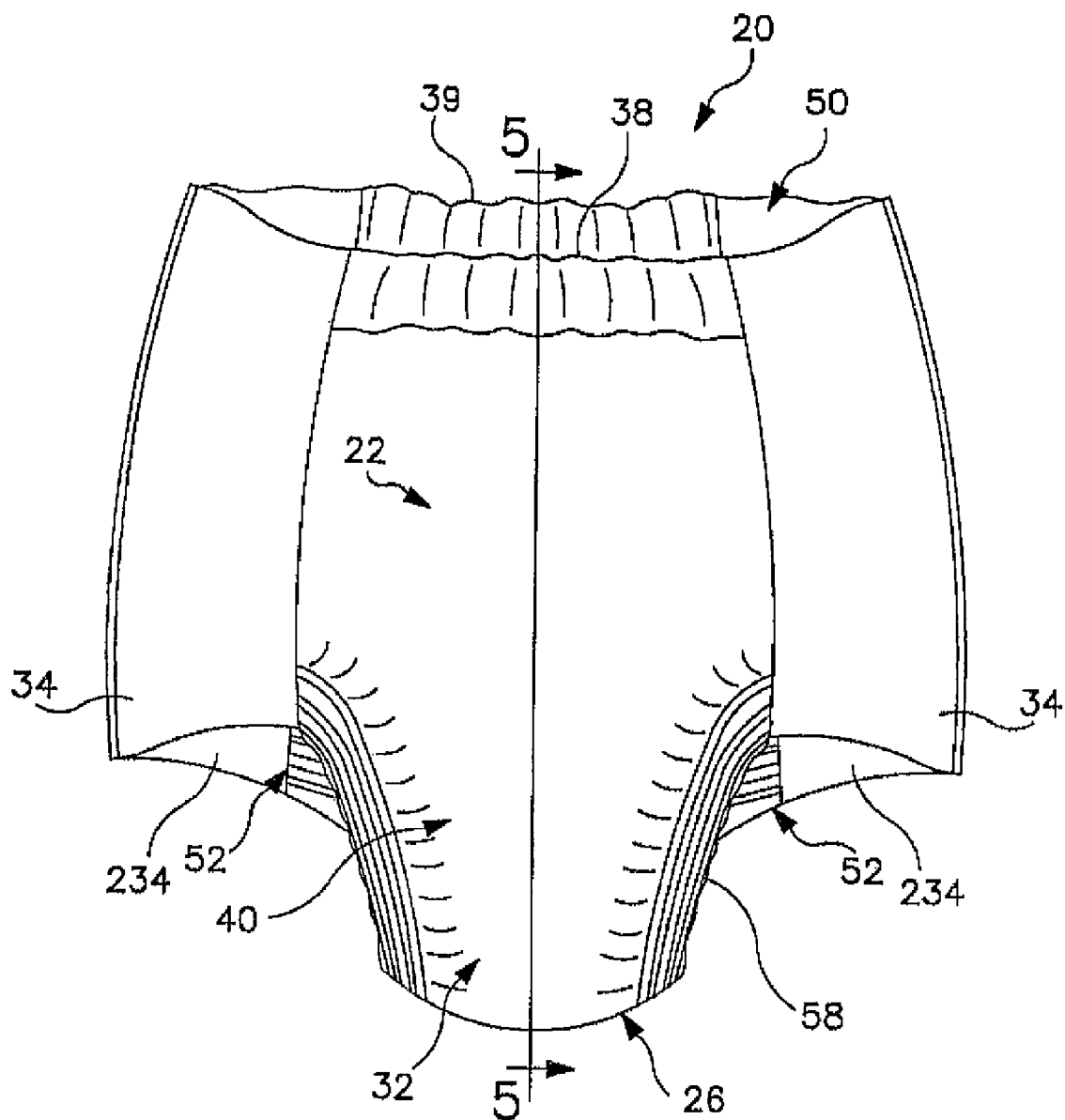
FIG. 1 is a perspective view of a pant-like absorbent garment, such as a training pant, having the optimized parameters of the invention.

Referring to FIG. 1, a pant-like absorbent article, such as a training pant 20, is illustrated. The training pant 20 includes a chassis 32 defining a front region 22, a back region 24, and a crotch region 26 interconnecting the front and back regions. The chassis 32 includes a body side liner 42 which is configured to contact the wearer, and an outer cover 40 opposite the body side liner which is configured to contact the wearer's clothing. An absorbent assembly 44 (FIG. 4) is positioned or located between the outer cover 40 and the body side liner 42.

Figure 2:
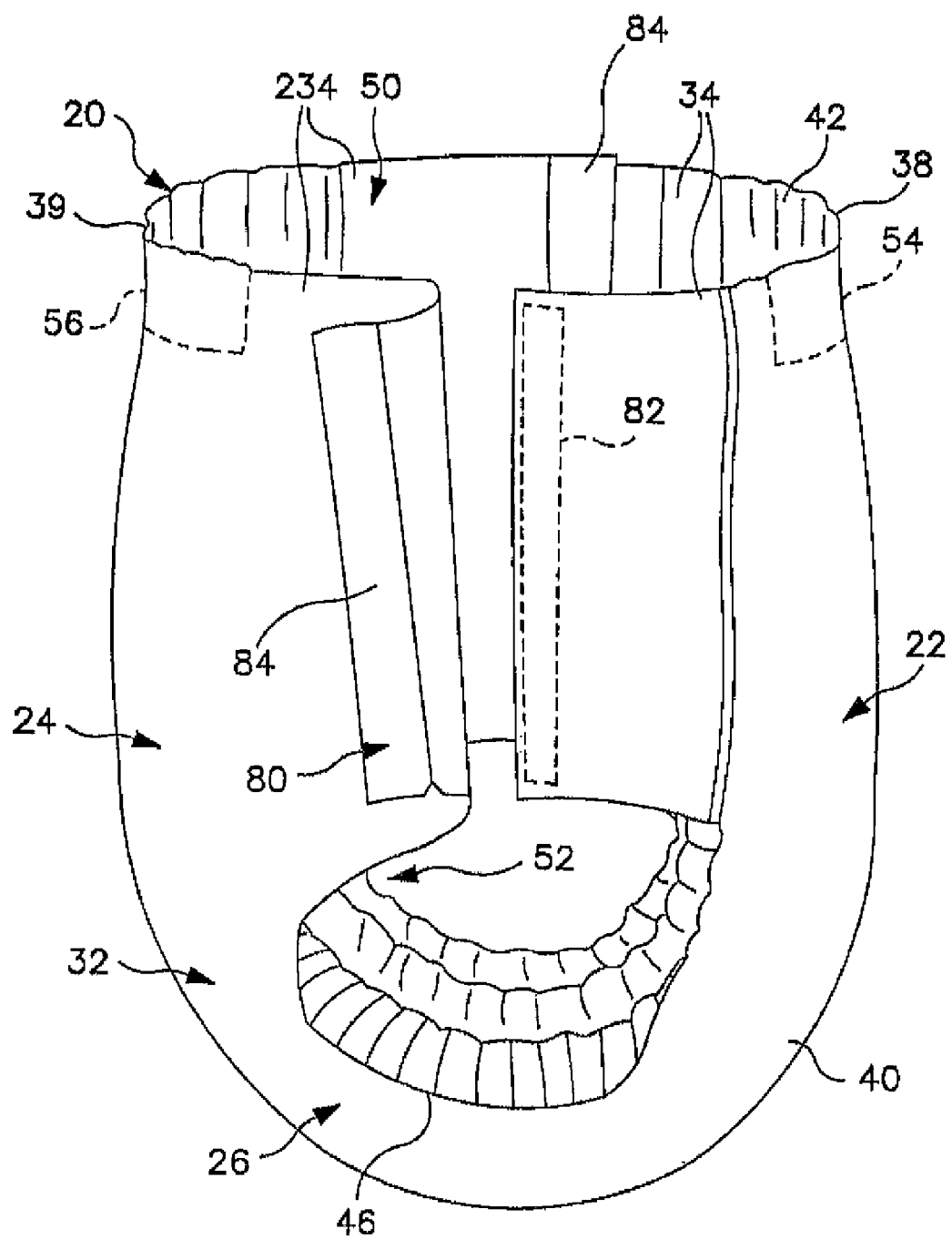
FIG. 2 is a perspective view of a pant-like absorbent garment with refastenable side seams, having the optimized parameters of the invention.

FIG. 2 illustrates a training pant 20, similar to the training pant 20 illustrated in FIG. 1 but having refastenable sides. A training pant 20 having permanently bonded sides, as shown in FIG. 1, or a training pant 20 having refastenable sides in the fastened position, as partially shown in FIG. 2, defines a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer.

As shown in further detail in FIGS. 3 and 4, the chassis 32 also defines a pair of longitudinally opposed waist edges, which are designated front waist edge 38 and back waist edge 39. The front region 22 is contiguous with the front waist edge 38, and the back region 24 is contiguous with the back waist edge 39. The waist edges 38, 39 are configured to encircle the waist of the wearer when worn and provide the waist opening 50 which defines the waist circumference dimension, as described below. For reference, arrows 48 and 49 depicting the orientation of the longitudinal axis and the transverse axis, respectively, of the training pant 20 are illustrated in FIGS. 3 and 4.

The illustrated absorbent chassis 32 includes a pair of transversely opposed front side panels 34, and a pair of transversely opposed back side panels 234. The side panels 34, 234 may be integrally formed with the outer cover 40 and/or the body side liner 42, or may include two or more separate elements.

In particular embodiments for improved fit and appearance, the side panels 34 and 234 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 234 desirably have an average length dimension of about 10 centimeters or greater, such as about 15 centimeters. While each of the side panels 34 and 234 extend from the waist opening 50 to one of the leg openings 52, the back side panels 234 have a continually decreasing length dimension moving in an outward transverse direction, as is best shown in FIGS. 3 and 4.

The side panels 34 and 234 desirably include an elastic material capable of stretching in a direction generally parallel to the transverse axis 49 of the training pant 20. Suitable elastic materials, as well as processes of incorporating side panels into a training pant, are known to those skilled in the art, and are described, for example, in U.S. Pat. No. 4,940,464 issued Jul. 10, 1990 to Van Gompel et al., which is incorporated herein by reference.

As mentioned, the training pant 20 according to the present invention may be refastenable, thereby including a fastening system 80 for securing the training pant about the waist of the wearer (FIG. 2). The illustrated fastening system 80 may include fastening components 82 that are adapted to refastenably connect to mating fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. In one embodiment, the outer cover material and/or the body side liner material may serve as a loop type fastener.

Hook type fasteners typically include a fabric or material having a base or backing structure and a plurality of hook members extending upwardly from at least one surface of the backing structure. Suitable single-sided hook materials for the fastening components 82 or the mating fastening components 84 are available from Velcro Industries B.V., Amsterdam, Netherlands or affiliates thereof. In one embodiment, the outer cover material and/or the body side liner material may serve as a hook type fastener.

The absorbent assembly 44 can be any structure which is generally compressible, conformable, non-irritating to the wearer's skin, and capable of absorbing and retaining liquids and certain body wastes at the levels discussed herein. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The absorbent assembly 44 can have variable thickness, with greater thickness in "target" areas, such as in a central portion of the crotch region. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 can include an extremely thin absorbent composite material sold under the trade name NOVATHIN® available from Rayonier Corporation located in Jessup, Ga., U.S.A., and/or an ultra-thin-absorbent (UTA) material including a mixture of SAP and pulp fiber. An example of a suitable UTA may include 3.7 grams (g) of FAVOR® SXM 9543 SAP, available from Stockhausen GmbH & Co. KG located in Krefeld, Fed. Rep. of Germany, and 3.7 g of NB416 pulp fiber available from Weyerhauser located in Federal Way.

In another embodiment, the absorbent assembly 44 can be generally rectangular in shape, and can include a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 0 to about 90 weight percent based on total weight of the absorbent assembly 44. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly 44.

The chassis 32 can also incorporate other materials that are designed primarily to receive, temporarily store, and/or transport liquid along the mutually facing surface with the absorbent assembly 44, thereby maximizing the overall absorbent capacity of the absorbent assembly 44, if desired. One suitable material is referred to as a surge layer The absorbent assembly 44, typically the most bulky component of a training pant 20, is relatively thin in the present invention. As a result, the overall thickness of the garment of the present invention, as measured according to the test method below, is less than about 4.5 millimeters (mm), or less than about 4 mm, or less than about 3 mm, or less than about 2 mm. Because the overall thickness of the garment is relatively small, the garment can possess the look and feel of underwear. Furthermore, due to the minimal bulkiness of the garment, the overall longitudinal length of the garment, measured from the front waist edge 38 to the back waist edge 39 as described in further detail in the test method below, can be shorter than bulkier garments while maintaining the same position and fit as bulkier garments. For example, most pant-like garments are worn with the front waist edge 38 resting in the area of the wearer's navel and the back waist edge 39 resting along the small of the wearer's back. Both a bulky garment and the garment of the invention can be worn in the same manner, stretching from the wearer's navel to the small of the wearer's back, while the bulky garment has a longitudinal length considerably larger than the longitudinal length of the garment of the invention.

Figure 5:
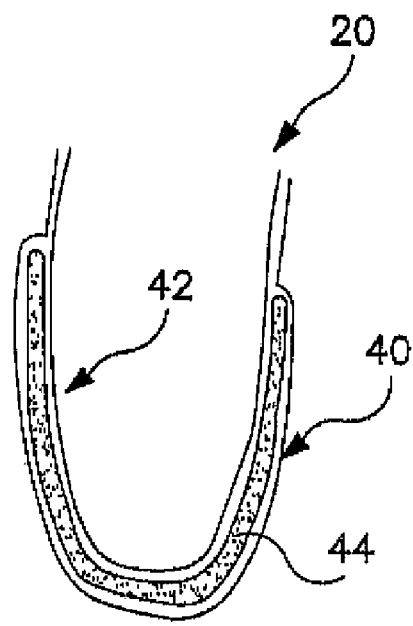
FIG. 5 is a cross-sectional view of the absorbent garment of FIG. 1 taken along line 5-5.
Figure 6:
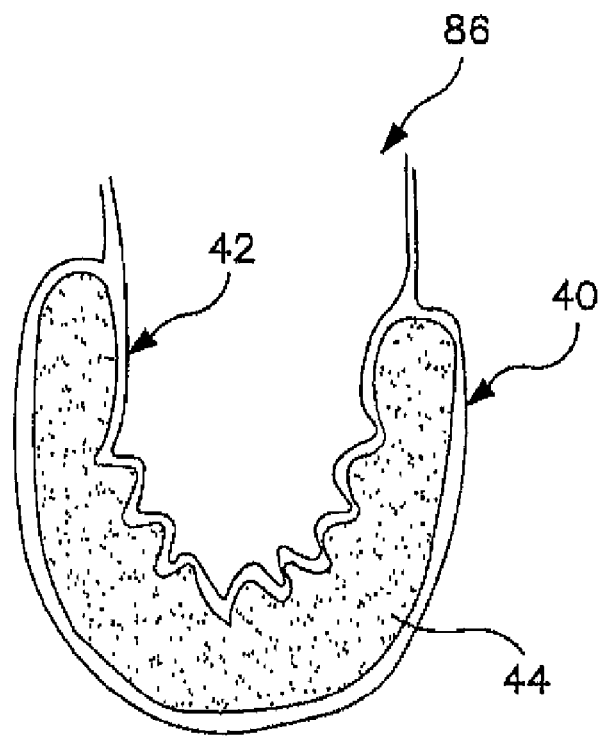
FIG. 6 is a cross-sectional view of a representational prior art absorbent garment from a view similar to the view of the garment in FIG. 5.

FIG. 5 is a cross-sectional view of the garment 20 of FIG. 1, showing the thin absorbent layer 44 between the outer cover 40 and the body side liner 42. As can be seen in FIG. 5, very little excess length is added to the outer cover 40 and to the body side liner 42 to envelop the absorbent layer 44. In contrast, FIG. 6 shows a representational prior art absorbent garment 86 from the same view as in FIG. 5, in which it is apparent that the outer cover 40 and the body side liner 42 must be longer in the prior art garment 86 than in the garment 20 in order to encompass the thick absorbent layer 44 while covering the same length of the wearer's body as the garment 20 of the invention covers.

Training pants and other pant-like absorbent garments are typically marketed in sizes that correspond to an intended wearer's weight. For purposes of describing the garment 20 of the present invention in terms of size independent of the intended wearer, the garment size is described in terms of the circumference of the waist opening 50. A method for determining the waist circumference (at 500 grams tension) is described in detail below. In the garment 20 of the present invention, the circumference of the waist opening 50 may be in a range of between about 450 mm and about 750 mm, or between about 500 mm and about 700 mm.

The garment 20 of the invention has been configured in a manner that provides desirable product features and the resulting product has been found to have a certain relationship between the longitudinal length and the waist circumference. More specifically, the garment 20 of the invention has a longitudinal length of the absorbent chassis 32 that is proportional to the waist circumference of the chassis 32 in a linear relationship that does not hold true for currently available commercial training pants. The longitudinal length of the training pant 20 can be measured according to the method described in detail below. In the garment 20 of the present invention, the longitudinal length of the garment may be in a range of between about 350 mm and about 650 mm, or between about 375 mm and about 600 mm, or between about 400 mm and about 575 mm.

Figure 7:
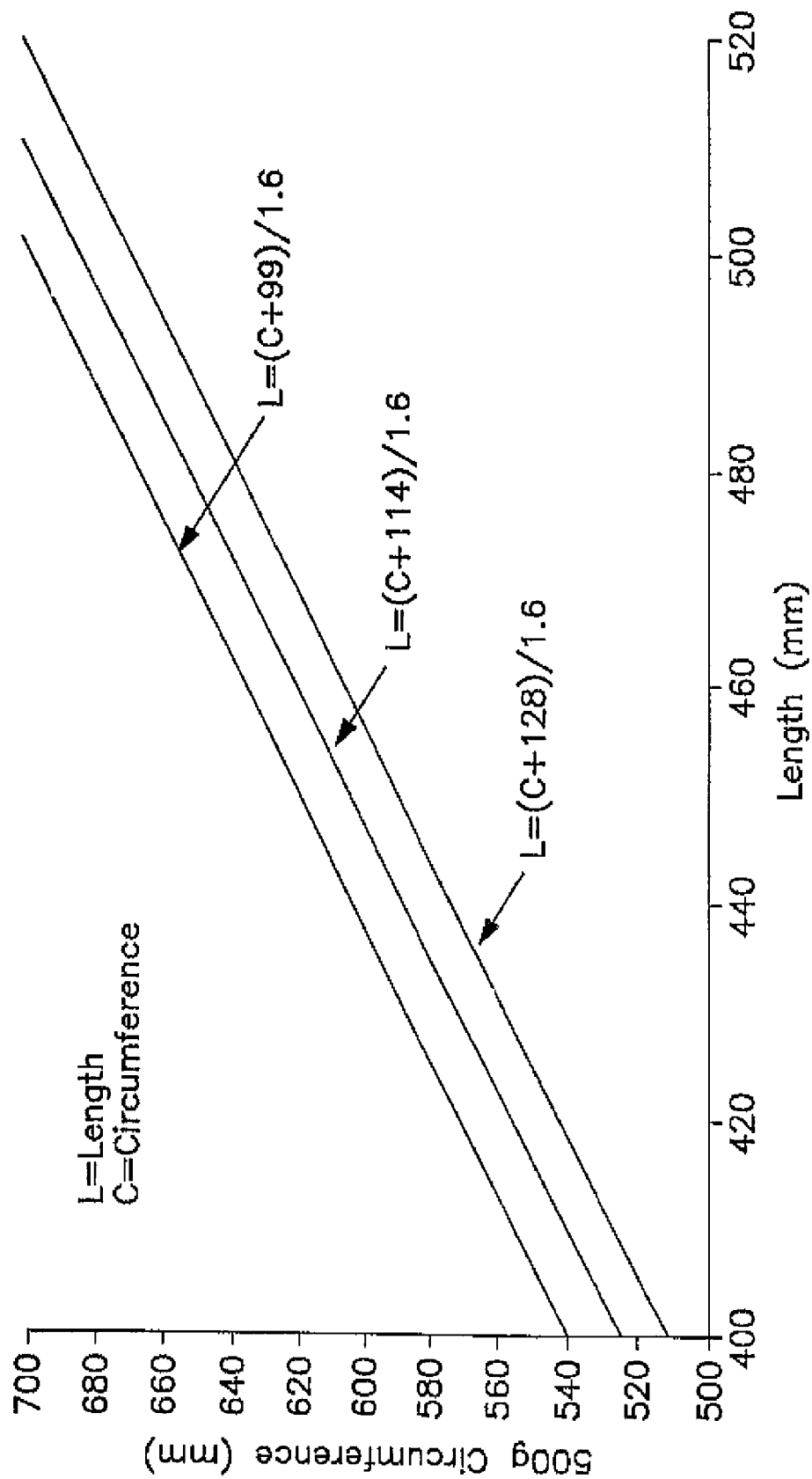
FIG. 7 is a graphical representation of the optimized parameters of several embodiments of the invention.

As illustrated in FIG. 7, a linear relationship can be drawn between the longitudinal length (x) and the waist circumference (y) in accordance with the well-known equation of a line:

$$y = mx + b \tag{1}$$

wherein m is the slope of the line and b is the y-intercept of the line. Isolating the longitudinal length variable, the equation becomes:

$$\text{Length} = (\text{Circumference} - b)/m \tag{2}$$

Equation 2 is used to determine the maximum length of the garments of the invention. Thus, the equation is more accurately written as:

$$\text{Length} \leq (\text{Circumference} - b)/m \tag{3}$$

As represented in Equation 3, the range of length and circumference relationships exists above the line.

In each of the embodiments of the invention, the slope (m) is approximately 1.6. In one embodiment of the invention, the y-intercept is −128, resulting in the following equation:

$$\text{Length} \leq (\text{Circumference} + 128)/1.6 \tag{4}$$

In another embodiment of the invention having a lower maximum length, the y-intercept is −114, resulting in the following equation:

$$\text{Length} \leq (\text{Circumference} + 114)/1.6 \tag{5}$$

In another embodiment of the invention having an even lower maximum length, the y-intercept is −99, resulting in the following equation:

$$\text{Length} \leq (\text{Circumference} + 99)/1.6 \quad (6)$$

The relationship between length, circumference, and thickness is a three-dimensional relationship, but can be approximated in a two-dimensional form with the thickness dimension superimposed over the linear relationship between length and circumference. As a result, shown in FIG. 7, the thickness is substantially constant along each of the lines defining the length and the circumference parameters, and decreases as the y-intercept increases. However, because the thickness is superimposed from a three-dimensional state onto the two-dimensional graph, the lines, in addition to representing the length/circumference relationship, represent shadows of the thickness parameters rather than actual thickness parameters. Thus, in FIGS. 8-10 in the Example below, the labels of approximate thicknesses are merely approximations and cannot be represented precisely in a two-dimensional form.

Equations 3-6 can be used in a process for making the garment 20 of the invention. More particularly, once a desired waist circumference has been determined, the circumference can be substituted into Equation 3, along with a desired slope (m) and y-intercept (b), to determine an appropriate longitudinal length of the garment. Equations 4-7 provide suggested slope and y-intercept values, namely a slope of 1.6 and a y-intercept of −128, −114, or −99. Once the desired longitudinal length has been determined, the garment 20 can be made.

The garment 20 of the invention suitably has a saturated capacity of between about 100 and about 800 grams, or between about 150 and about 600 grams, or between about 200 and about 500 grams. The saturated capacity of the garment can be measured according to the test method described in detail below.

The garment 20 of the invention suitably has an edge compression peak load of less than about 1500 grams, or less than about 1200 grams, or less than about 800 grams. The edge compression peak load of the garment can be measured according to the test method described in detail below.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable body side liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain "non-breathable" elastic films can also be used to make the outer cover 40. Examples of suitable non-breathable films can be made of styrene-ethylene-butylene-styrene or styrene-isoprene-styrene block copolymers, KRATON polymers from Kraton Polymers USLLC of Belpre, Ohio, U.S.A., metallocene catalyzed elastomers or plastomers, and the like. Other materials suitable for making the outer cover 40 include monolithic breathable films, such as those made of polyether amide based polymers, for example PEBAX, and ether/ester polyurethane thermal-plastic elastomers.

The liquid permeable body side liner 42 is illustrated as overlying the outer cover 40 and absorbent assembly 44, and may but need not have the same dimensions as the outer cover 40. The body side liner 42 is desirably compliant, soft feeling, and non-irritating to the wearer's skin. Further, the body side liner 42 can be less hydrophilic than the absorbent assembly 44, to present a relatively dry surface to the wearer and permit liquid to readily penetrate through its thickness.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 available from available from Uniqema Inc., a division of ICI of New Castle, Del., U.S.A. and GLUCOPON® 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and body side liner 42 can include elastomeric materials, it can be desirable in some embodiments for the composite structure to be generally inelastic, where the outer cover, the body side liner and the absorbent assembly include materials that are generally not elastomeric.

To further enhance containment and/or absorption of body exudates, the training pant 20 may include a front waist elastic member 54, a rear waist elastic member 56, and leg elastic members 58, as are known to those skilled in the art (FIG. 4). The waist elastic members 54 and 56 can be operatively joined to the outer cover 40 and/or body side liner 42 along the opposite waist edges 38 and 39, and can extend over part or all of the waist edges. The leg elastic members 58 are desirably operatively joined to the outer cover 40 and/or body side liner 42 along opposite side edges of the chassis 32 and positioned in the crotch region 26 of the training pant 20.

The waist elastic members 54, 56 and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

To enhance containment and/or absorption of any body exudates discharged from the wearer, the chassis 32 may include a pair of containment flaps 46 which are configured to provide a barrier to the transverse flow of body exudates. A flap elastic member 53 (FIG. 4) may be operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the chassis 32, and can extend longitudinally along the entire length of the chassis or may only extend partially along the length of the chassis. Suitable constructions and arrangements for the containment flaps 46 are generally well known to those skilled in the art.

As described herein, the various components of the absorbent garment 20 can be integrally assembled together employing various types of suitable attachment means, such as adhesive, sonic and thermal bonds or combinations thereof. The resulting product is a thin, flexible, disposable, absorbent garment that fits just like underwear. More particularly, the absorbent garment has a maximum length proportional to a maximum thickness relative to a waist circumference of the garment, while maintaining a considerable absorbent capacity.

EXAMPLE

The following Example provides a comparison between training pants having optimized parameters in accordance with the present invention and presently available commercial products. More specifically, this example provides a graphical representation of the training pants of the invention and of presently available commercial products with respect to the linear relationship that defines the training pants of the present invention.

Table 1 provides descriptions of the training pants tested in this Example, with codes 17-22 being experimental codes. Codes 17 and 20-22 are representative of the training pants of the present invention.

TABLE 1

Training Pants Tested

| Code | Product Name | Size | Gender | Manufacturer | Location Purchased | Date Purchased |
|---|---|---|---|---|---|---|
| 1 | TARGET ® training pants | M | Unisex | Paragon | USA | September 2000 |
| 2 | TARGET ® training pants | L | Unisex | Paragon | USA | September 2000 |
| 3 | EASY-UPS ® | M | Unisex | Procter & Gamble | USA | March 2002 |
| 4 | EASY-UPS ® | L | Unisex | Procter & Gamble | USA | March 2002 |
| 5 | EASY-UPS ® | XL | Unisex | Procter & Gamble | USA | March 2002 |
| 6 | Libero Up & Go | Maxi | Unisex | SCA | Holland | June 2001 |
| 7 | Libero Up & Go | Maxi+ | Unisex | SCA | Holland | June 2001 |
| 8 | Libero Up & Go | XL | Unisex | SCA | Holland | June 2001 |
| 9 | Libero Up & Go | XL+ | Unisex | SCA | Holland | June 2001 |
| 10 | Mooney Man | M | Boy | Uni Charm | Japan | August 2000 |
| 11 | Mooney | L | Boy | Uni Charm | Japan | August |

TABLE 1-continued

Training Pants Tested

| Code | Product Name | Size | Gender | Manufacturer | Location Purchased | Date Purchased |
|------|--------------|------|--------|--------------|--------------------|-----------------|
| 12 | Man Mooney | XL | Girl | Uni Charm | Japan | August 2000 |
| 13 | Man Torepan | | Girl | Uni Charm | Japan | August 2000 |
| 14 | Man PULL-UPS ® | M | Unisex | Kimberly-Clark | USA | January 2002 |
| 15 | PULL-UPS ® | L | Unisex | Kimberly-Clark | USA | January 2002 |
| 16 | PULL-UPS ® | XL | Unisex | Kimberly-Clark | USA | January 2002 |
| 17 | Experimental A | M | Unisex | Kimberly-Clark | | |
| 18 | Experimental B | L | Unisex | Kimberly-Clark | | |
| 19 | Experimental C | XL | Unisex | Kimberly-Clark | | |
| 20 | Experimental D | L-XL | Unisex | Kimberly-Clark | | |
| 21 | Experimental E | L-XL | Unisex | Kimberly-Clark | | |
| 22 | Experimental F | L-XL | Unisex | Kimberly-Clark | | |

Experimental codes A, B, and C (codes 17-1) each included the same composition and design with the only differences being the sizes. More particularly, these codes were made up of the same components as a PULL-UPS® training pant, but with ultra-thin absorbent layers in place of the original absorbent layers. These ultra-thin absorbent layers are taught in U.S. patent application Ser. No. 09/939,061 filed 24 Aug. 2001, herein incorporated by reference. More specifically, Experimental code A (code 17) included an ultra-thin absorbent made up of 12.0 g FAVOR 9543 superabsorbent material, available from Stockhausen GmbH & Co., and 9.8 g ND416 pulp, available from Weyerhaeuser of Federal Way, Wash., U.S.A., Experimental code B (code 18) included an ultra thin absorbent made up of 12.9 g FAVOR 9543 superabsorbent material and 10.5 g ND416 pulp, and Experimental code C (code 19) included an ultra thin absorbent made up of 13.5 g FAVOR 9543 superabsorbent material and 11.1 g ND416 pulp.

Experimental code D (code 20) was a refastenable training pant with all-around stretch. The pant had an outer cover made up of a monolithic breathable film laminated between two 0.3 osy polypropylene spunbond facings that were necked and creped, and a body side liner made up of necked and creped polypropylene spunbond. Between the outer cover and the body side liner was a 450 gsm absorbent layer made up of a coformed material of 10% KRATON 2760 meltblown filament available from Kraton Polymers, 15% Sulfitate HJ pulp available from Rayonier Corporation of Jessup, Ga., U.S.A, and 75% FAVOR 880 superabsorbent material available from Stockhausen GmbH & Co. The pant also included containment flaps, waist elastics, leg elastics, and fasteners, all in accordance with the described invention.

Experimental code E (code 21) was a non-refastenable training pant having an outer cover made up of the same components as a PULL-UPS® training pant, but with an ultra-thin absorbent layer in place of the original absorbent layer, similar to the ultra-thin absorbent layers in codes 17-19, including 3.9 g FAVOR 9543 superabsorbent material and 3.9 g ND416 pulp and having a basis weight of 225 gsm.

Experimental code F (code 22) was a non-refastenable training pant, similar to code E (code 21), but having a 29.5 g 400 gsm NOVATHIN Composite 4000160 absorbent layer, available from Rayonier, in a maximized area.

Each of the training pants listed in Table 1 were tested for longitudinal length, front thickness, waist circumference, and saturated capacity, in accordance with each of the test methods provided below. Each of the tests were performed on five samples of each product, and the averages of the results are provided in Table 2.

TABLE 2

Parameters of the Training Pants Listed in Table 1

| Code | Length (mm) | Thickness (mm) | Waist Circumference at 500 g (mm) | Saturated Capacity (g/g) |
|------|-------------|----------------|-----------------------------------|--------------------------|
| 1 | 457 | 6.66 | 543 | 384 |
| 2 | 486 | 8.42 | 544 | 498 |
| 3 | 450 | 10.09 | 539 | 508 |
| 4 | 466 | 10.55 | 556 | 533 |
| 5 | 492 | 9.27 | 599 | 620 |
| 6 | 427 | 6.31 | 514 | 516 |
| 7 | 450 | 6.38 | 575 | 520 |
| 8 | 483 | 7.16 | 577 | 668 |
| 9 | 484 | 7.56 | 582 | 725 |
| 10 | 421 | 6.24 | 527 | 416 |
| 11 | 462 | 6.01 | 566 | 468 |
| 12 | 500 | 5.36 | 614 | 577 |
| 13 | 458 | 4.13 | 542 | 130 |
| 14 | 459 | 6.85 | 580 | 440 |
| 15 | 505 | 6.81 | 626 | 546 |
| 16 | 516 | 6.85 | 686 | 517 |
| 17 | 441 | 4.39 | 575 | 388 |
| 18 | 486 | 4.76 | 613 | 396 |
| 19 | 515 | 4.41 | 679 | 443 |
| 20 | 467 | 3.37 | 649 | 684 |
| 21 | 461 | 2.44 | 668 | 154 |
| 22 | 474 | 1.57 | 673 | 479 |

Figure 8:
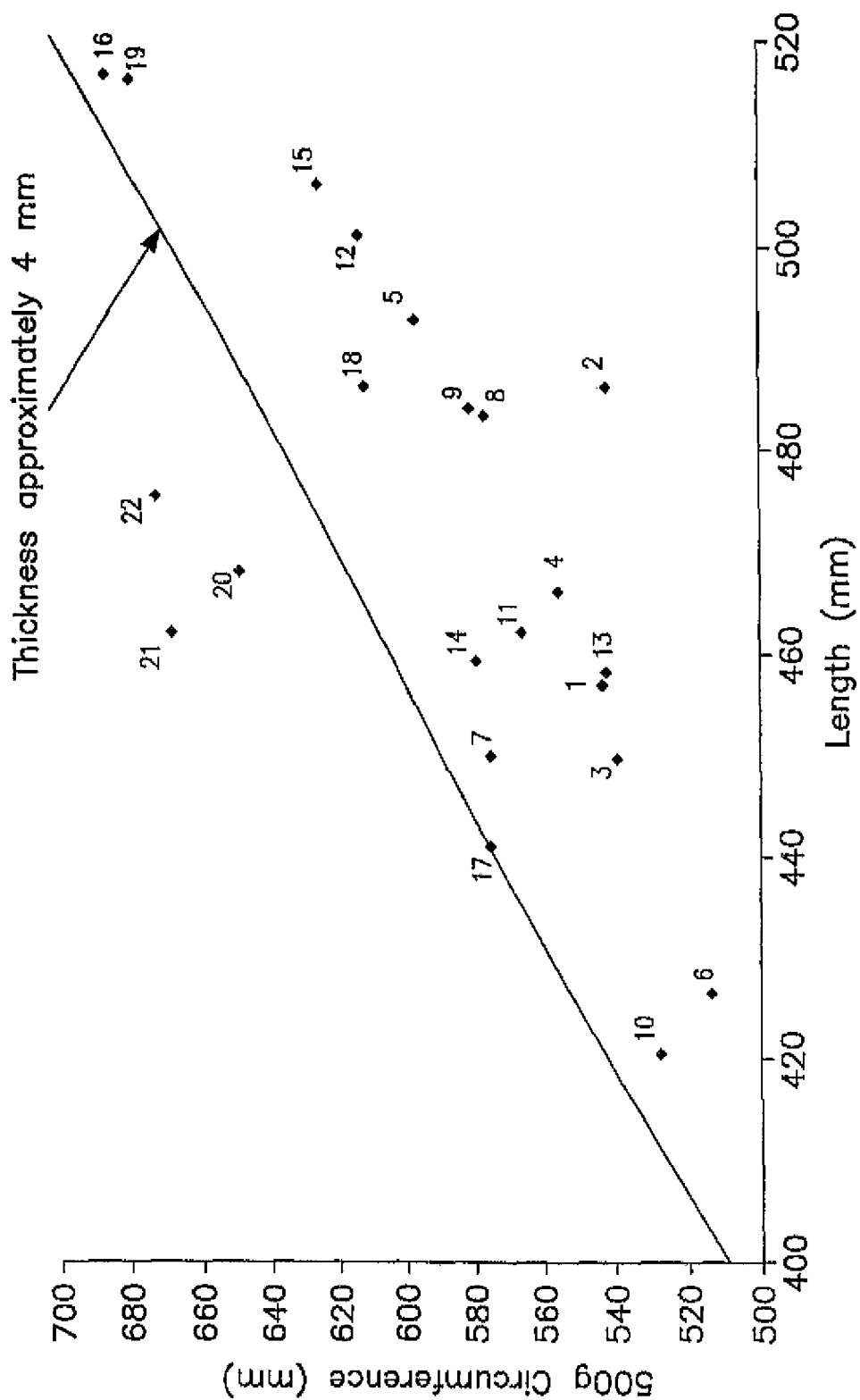
FIG. 8 is a graphical representation of the optimized parameters of one embodiment of the invention with a number of test codes imposed thereon.

The data from Table 2 is provided in FIG. 8, with the line across the graph and the area above the line representing the embodiment of the invention in which the longitudinal length is proportional to the circumference of the waist opening according to the relation:

Length≦(Circumference+128)/1.6

As indicated in FIG. 8, the thickness of the garments along the line is approximately 4 mm, with the garments in the area above the line having even smaller thicknesses.

Figure 9:
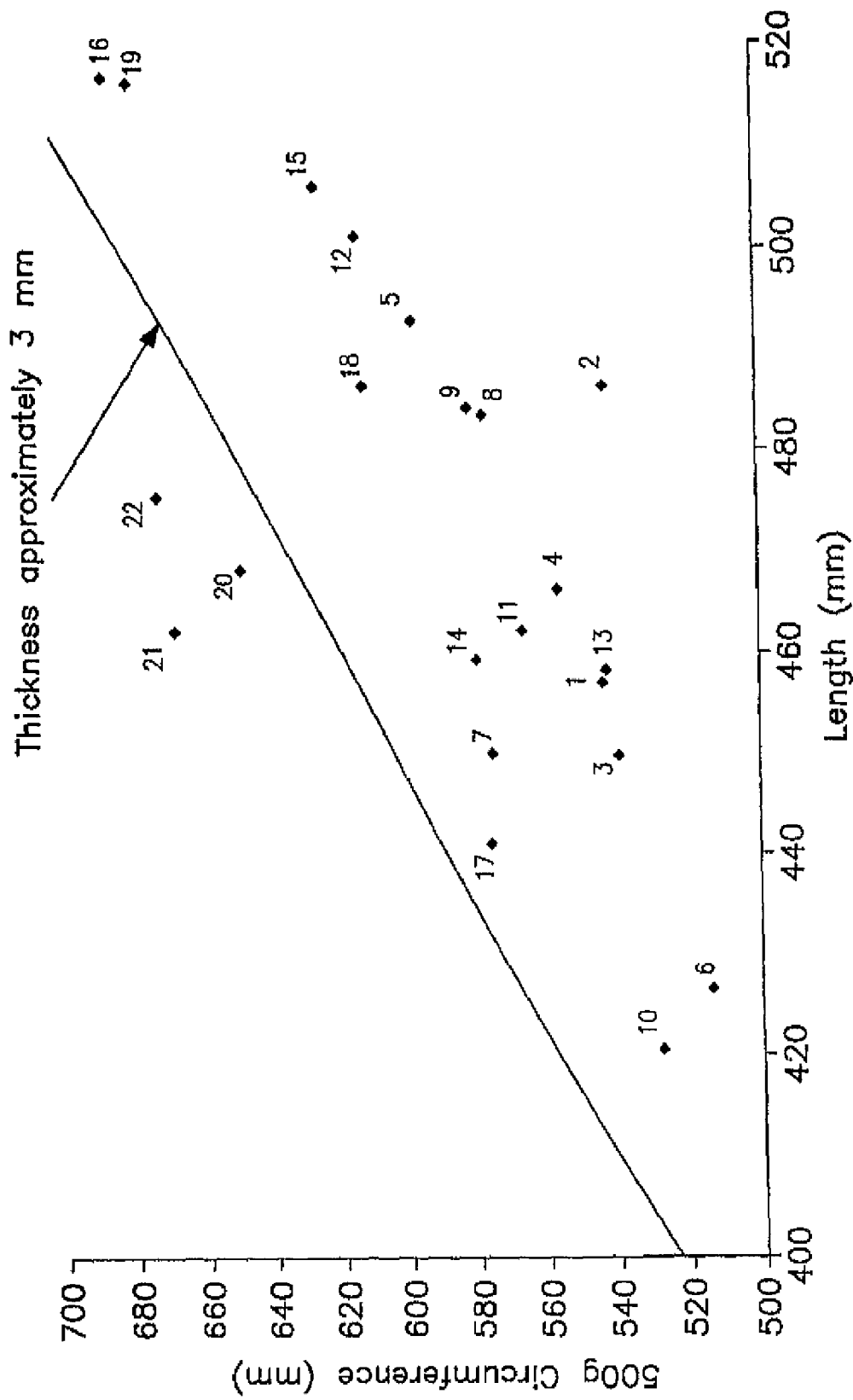
FIG. 9 is a graphical representation of the optimized parameters of another embodiment of the invention with a number of test codes imposed thereon.

Similarly, the data from Table 2 is also provided in FIG. 9, with the line across the graph and the area above the line representing the embodiment of the invention in which the longitudinal length is proportional to the circumference of the waist opening according to the relation:

Length≦(Circumference+114)/1.6

Figure 10:
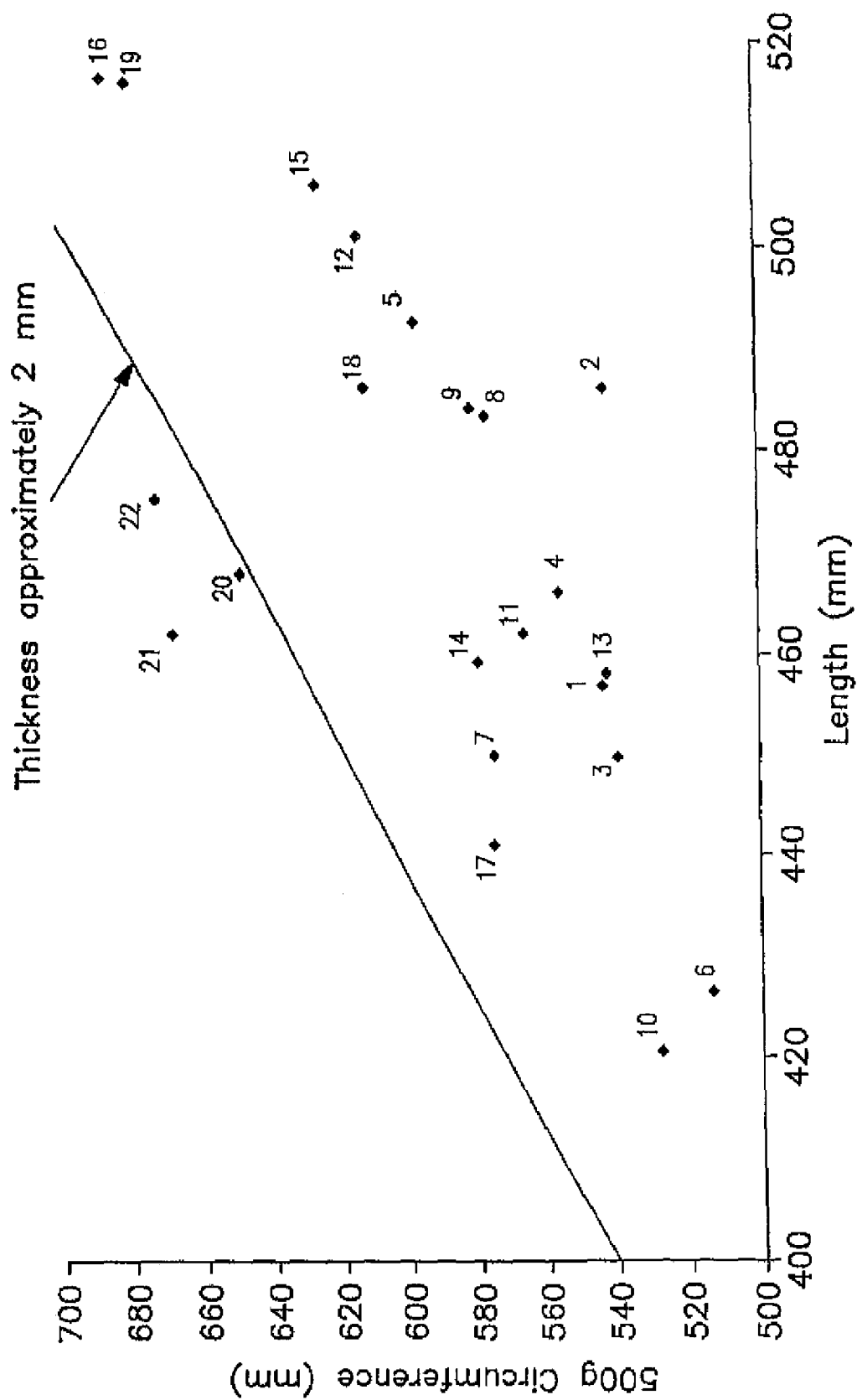
FIG. 10 is a graphical representation of the optimized parameters of yet another embodiment of the invention with a number of test codes imposed thereon.

As indicated in FIG. 9, the thickness of the garments along the line is approximately 3 mm The data from Table 2 is also provided in FIG. 10, with the line across the graph and the area above the line representing the embodiment of the invention in which the longitudinal length is proportional to the circumference of the waist opening according to the relation:

Length≦(Circumference+99)/1.6

As indicated in FIG. 10, the thickness of the garments along the line is approximately 2 mm.

TEST METHODS

Thickness Measurement Test Method

A whole absorbent product can be measured for thickness in the thickest part of the product, usually in the target zone that is intended to receive liquid insults. When measured by the method described below, such a product suitably may have a dry thickness ($t_i$) of less than about 4.5 mm, more suitably less than about 4.0 mm, even more suitably less than about 3.0 mm, most suitably less than about 2.0 mm. For example, in one embodiment of this invention, the absorbent garment may have a dry thickness of about 0.5 to about 3.0 mm.

If the sample exhibits greatest thickness in the target region of the product, the sample can be tested in this location by the following method. Samples with greater thickness outside the target region should be tested in the location of greatest thickness.

The sample to be tested is folded in half as for wearing, with front and back waist edges aligned. The liner of the product is marked at the fold line. The product is opened and laid flat, and the front region of the absorbent is marked halfway between the marked fold and the front edge of the absorbent, along the longitudinal centerline of the product. If the product is closed (such as with side seams), the seams are opened so that the product can be laid flat. Elastics (such as along leg borders or in containment flaps) are removed if possible, or cut in several places to permit the absorbent to lie flat in an uncontracted state.

The sample is tested for dry thickness at the marked point on the front of the absorbent, forward of the marked fold line. The intact product is gently spread flat to remove any wrinkles at this location, but is not stretched. The product is placed underneath a 0.2 pounds per square inch (psi) weight, and the thickness of the product in this region is recorded. A suitable tester for absorbent thickness is a MITUTOYO 543 Series thickness gauge, available from Mitutoyo-MTI Corporation, Japan, equipped with a 3 inch diameter brass foot that applies a weight of 0.2 psi. Five specimens per sample are tested, and the results are averaged to provide a thickness value for that sample.

Longitudinal Length Measurement Test Method

The product (20) has a length dimension measured between the front and back end edges (38 and 39) along the longitudinal axis (48). The length dimension of the product (20) is determined.

A suitable method for determining the longitudinal length of the product (20) is to hang the product vertically adjacent a flat, vertical surface. Prior to hanging, the product is opened by cutting or opening any side seams. Any elastic components that run the length of the chassis (such as leg elastics or elastics within containment flaps) are severed at least once per inch along their entire length. The product is hung with the back region (24) above the front region (22) and with the surface intended to face the wearer's outer garments during use positioned toward the flat, vertical surface. The top end margin of the product is held horizontal with two clamps, the inner edges of which are spaced 3.5 inches (8.9 cm) apart. The clamps are positioned if possible to avoid any absorbent within the product, and are symmetrically disposed with respect to the longitudinal centerline/axis of the product. Any waist elastic present in the product is not stretched prior to securing the clamps.

The lower end of the hanging product (front waistband region) is clamped with a jig weighing 250 g. The jig possesses two clamp units (medium size, Bulldog clips, 2⅛ inch) attached to a tie rod (¼-inch–20×12 inches, coarse thread, zinc plated), the clamps symmetrically placed with respect to the longitudinal centerline of the product, with a spacing between internal edges of the clamps of 3.5 inches (8.9 cm), with a ¼-inch nut placed at the inner and outer edges of each clamp to hold the clamps in place. One (capped) bottle (1-ounce plastic screw cap bottle, such as NALGENE brand) is attached to each clamp with a piece of string. The assembly is placed on a laboratory balance and lead shot (No. 5 chilled lead shot, such as LAWRENCE brand) is added to each bottle (in equal amounts) until the total weight of the jig is as close to 250 grams as possible. The jig is attached to the lower end of the hanging product, as mentioned above.

For a typical product, a load of 250 g is appropriate. The elongate length is then determined by measuring the distance between the front and back end edges (38 and 39) along the longitudinal centerline/axis (48), between the clamps. Five specimens of each code are analyzed, and the results for each code are averaged.

Waist Circumference Measurement Test Method

This procedure is a single-cycle tension bench test to measure waistband circumference of a test pant. The pant is tested in the state in which it is provided to the consumer, intended for immediate donning. The procedure measures waistband circumference under moderate tension after the waistband has been subjected to higher tension. A test pant is cycled to a specific loading rather than to a fixed elongation/extension.

Figure 11:
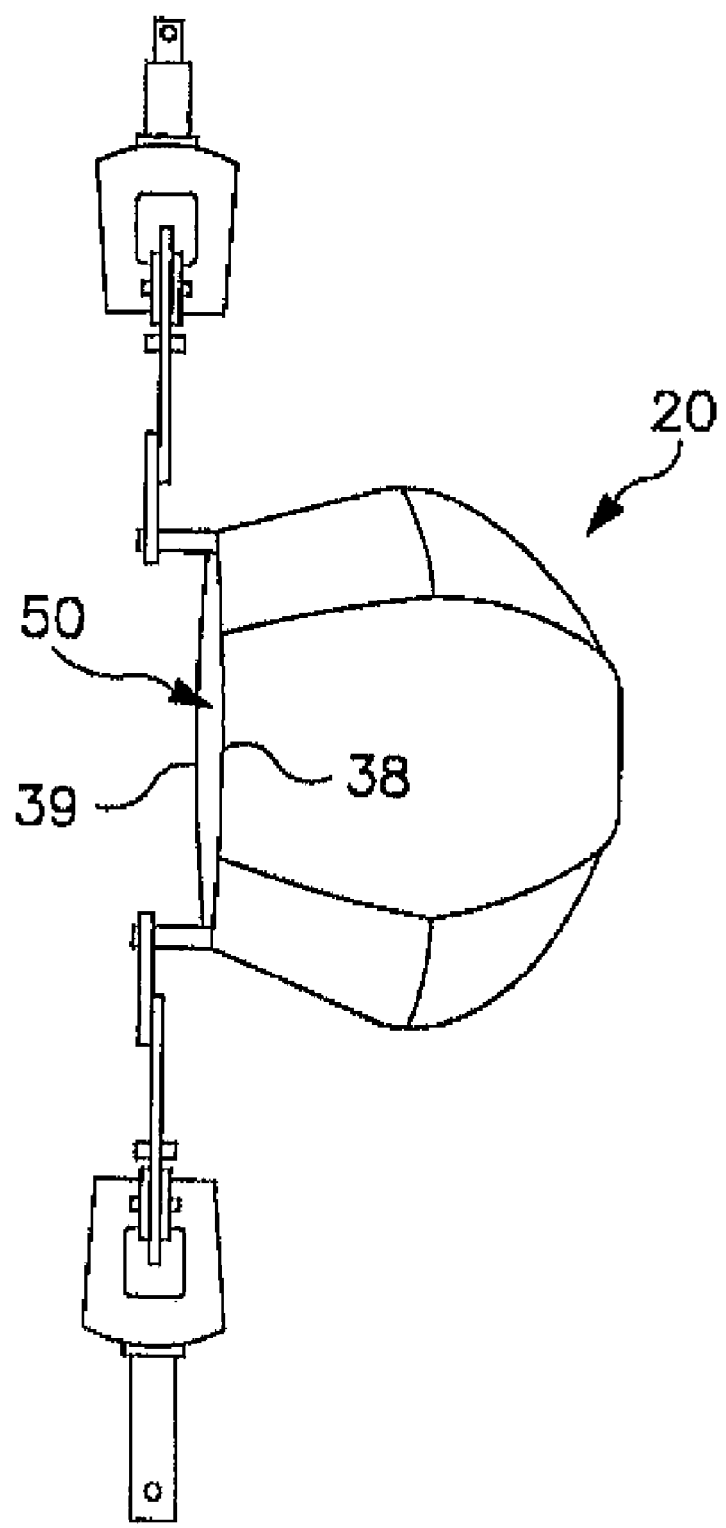
FIG. 11 illustrates a pant of the type shown in FIG. 1 disposed on a tensile tester to measure waist circumference.

Data generated by this test method includes:
Waistband circumference (mm) at an initial load of 70 g.
Waistband circumference (mm) at an intermediate load of 2000 g.
Waistband circumference (mm) at a final load of 500 g.
1. Overview A pant is placed on the upper and lower pins in position to measure the waistband gage length, as shown in FIG. 11.

Each pin is inserted one inch (2.5 cm) into the waist section of the pant. If the pant slips on the pins, clips may be applied to hold the pant firmly in place on the pins; care should be taken to avoid placing clips onto parts of the waistband that do not pass over the pins. The gage length is selected for the waist opening of the pant being tested, so as to provide a tension of between 0 and 65 grams (g) when the pant is positioned for the test, prior to the start of the test. The term "tension" refers to the gram value measured by the load cells in the tensile tester.

The jaws are separated until a load of 70 grams of tension is attained, at which tension the gage length is recorded. Then the jaws continue to move apart until 2,000 grams of tension is reached, at which tension the gage length is again recorded. The jaws then move immediately back together until a tension of 500 grams is reached, at which tension the gage length is again recorded. The standard test is one cycle per pant. The circumference at a given tension may be calculated using the gage length and the circumference value(s) for the upper and lower pins. Desirably at least five specimens are tested. The waistband circumference values at 500 grams tension from each specimen tested are averaged to obtain an average waistband circumference for a given sample.

Figure 12:
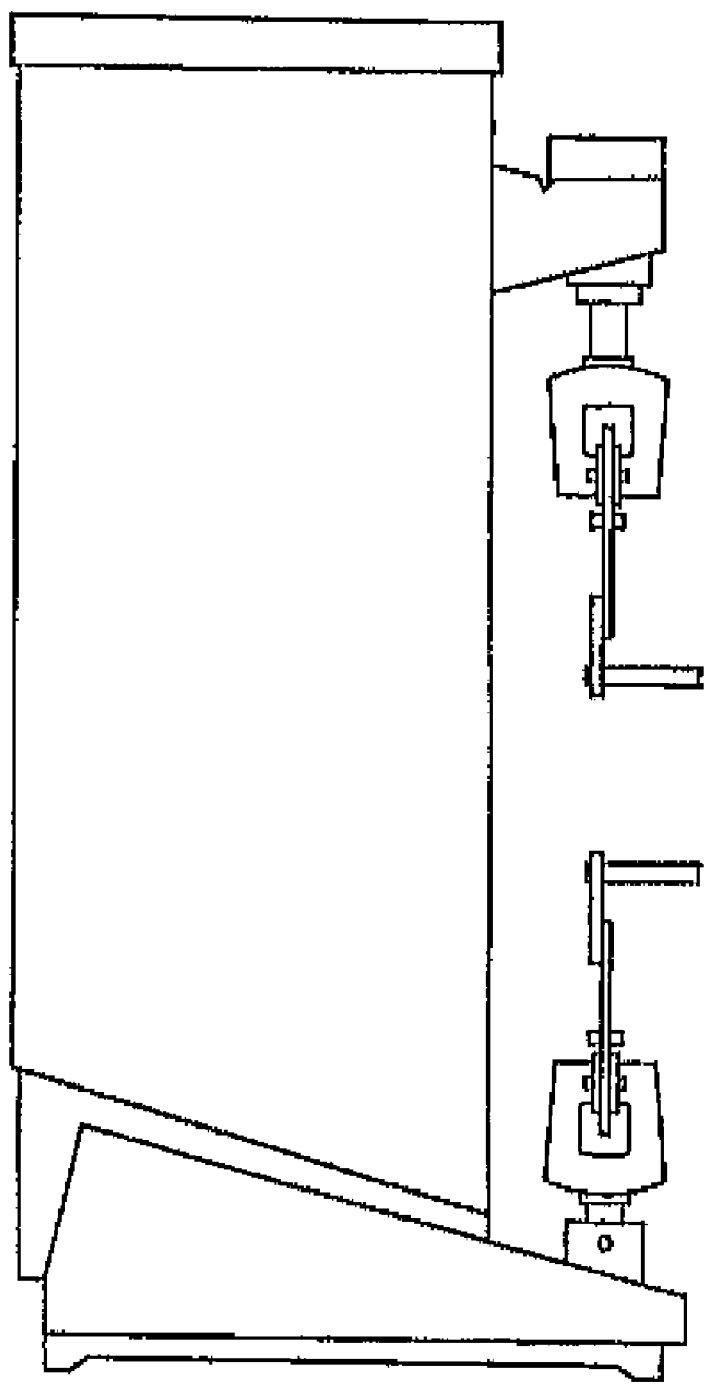
FIG. 12 illustrates a side view of a tensile tester used to measure waist circumference, as shown in FIG. 11.

FIG. 12 illustrates a side view of a tensile tester used to measure waistband circumferences of pants according to the present invention. FIG. 11 illustrates a pant of the type shown in FIG. 1 disposed on the tensile tester to measure the waistband circumference.

2. Apparatus and Materials 2.1 Constant Rate of Extension (CRE) tensile tester: MTS tensile tester model Synergie 200 Test Bed; available from MTS® Systems Corporation, Research Triangle Park, N.C. USA.

2.2 Load cells: A suitable cell selected so the majority of the peak load values fall between the manufacturer's recommended ranges of load cell's full scale value; Model 100N available from MTS® Systems Corporation, Research Triangle Park, N.C. USA.

2.3 Operating software and data acquisition system: MTS TestWorks® for Windows software version 4.06A, build 617; available from MTS® Systems Corporation, Research Triangle Park, N.C. USA.

2.4 Grips: pneumatic-action grips, top and bottom, identified as part number 2712-003 available from Instron Corporation, Canton, Mass. USA.

2.5 Grip faces: 25 by 75-mm (1 by 3-inch), suitable for holding pins.

2.6 Pins: rigid pins having a length of 6.3 centimeters (2.5 inch) and a knurled portion at one end for holding specimens, the knurled portion having an outside diameter of 6.4 millimeters (0.25 inch) and a length of 3.2 centimeters (1.25 inch).

2.7 Clips (optional): 1.9 cm. wide by 0.95 cm. capacity (¾" wide by ⅜" capacity) binder clips; part no. BTM00251 available from BT Office Products, Milwaukee, Wis., USA.

3. Conditioning

Conduct test in standard ASTM laboratory conditions: atmosphere of 23±2° C. (73.4±3.6° F.) and 50±5% relative humidity. The products should be measured after they equilibrate to laboratory conditions.

4. Test Specimen

No preparation needed. The whole pant is tested.

5. Procedure

Tensile Tester test conditions
Data acquisition rate . . . 100.0 Hz
Perform PreLoad (PreCond)? . . . No
Perform PreConditioning? . . . No
Perform PreLoad? . . . No
Cross head speed: . . . 500 mm/min
Gage length: . . . Appropriate starting gage length settings for both hip and waistband are those that will generate initial loads of between 0 and 65 g in a previously untested product
Go to load (cycle trigger) . . . 2000 g (or a maximum load value that can be experienced by the sample without causing the sample to tear or otherwise come apart)
Number of cycles . . . 1
Break sensitivity: 90%

A. Install pin assemblies as depicted in FIG. 11.

B. Using the tensile frame pushbutton controls for crosshead position, move pins so that the pant can be mounted on the pins without stretching the pant. Determine the gage length by measuring from the centerline of the first pin to the centerline of the second pin. Calibrate the software to this initial gage length.

C. Place the waistband onto the knurled section of the top pin. Center one side of the pant on top of the pin. Use a single binder clip to hold the pant at the waist opening in place on the pin; do not stretch the pant during application of the clip.

D. Click on ZERO to tare the load of the pant. Only tare the weight of the first pant for each sample population, not for each specimen.

E. Place the waistband on the opposite side of the pant on the bottom pin and clip in place as for the first pin. Adjust pant so both top and bottom pins are inserted 2.5 centimeters (1 inch) into the pant.

F. Using the tensile frame pushbutton controls for crosshead position, move pins apart until the load applied to the waistband is between 0 and 65 g.

G. Click on RUN button. The test will start automatically.

H. When the test is done, click on either FILE to save the data and graphs or NEXT to save only the data.

I. Remove the sample from the pins.

J. Repeat steps B, C and E through I for each specimen until the testing is complete.

The circumference of a measured waistband at any tension may be calculated by multiplying the gage length at that tension by 2, and adding one half the circumference of the upper pin and one half the circumference of the lower pin.

Modified Saturated Capacity Test Method

Saturated Capacity is determined using a Saturated Capacity (SAT CAP) tester with a Magnahelic vacuum gage and a latex dam. Referring to FIGS. 13-15, a Saturated Capacity tester vacuum apparatus 110 comprises a vacuum chamber 112 supported on four leg members 114. The vacuum chamber 112 includes a front wall member 116, a rear wall member 118 and two side walls 120 and 121. The wall members are about 0.5 inch thick, and are constructed and arranged to provide a chamber having outside dimensions measuring 23.5 inches in length, 14 inches in width and 8 inches in depth.

A vacuum pump (not shown) operably connects with the vacuum chamber 112 through an appropriate vacuum line conduit and a vacuum valve 124. In addition, a suitable air bleed line connects into the vacuum chamber 112 through an air bleed valve 126. A hanger assembly 128 is suitably mounted on the rear wall 118 and is configured with S-curved ends to provide a convenient resting place for supporting a latex dam sheet 130 in a convenient position away from the top of the vacuum apparatus 110. A suitable hanger assembly can be constructed from 0.25 inch diameter stainless steel rod. The latex sheet 130 is looped around a dowel member 132 to facilitate grasping and to allow a convenient movement and positioning of the latex sheet 130. In the illustrated position, the dowel member 132 is shown supported in a hanger assembly 128 to position the latex sheet 130 in an open position away from the top of the vacuum chamber 112.

A bottom edge of the latex sheet 130 is clamped against a rear edge support member 134 with suitable securing means, such as toggle clamps 140. The toggle clamps are mounted on the rear wall member 118 with suitable spacers 141 which provide an appropriate orientation and alignment of the toggle clamps 140 for the desired operation. Three support shafts 142 are 0.75 inches in diameter and are removably mounted within the vacuum chamber 112 by means of support brackets 144. The support brackets 144 are generally equally spaced along the front wall member 116 and the rear wall member 118 and arranged in cooperating pairs. In addition, the support brackets 144 are constructed and arranged to suitably position the uppermost portions of the support shafts 142 flush with the top of the front, rear and side wall members of the vacuum chamber 112. Thus, the support shafts 142 are positioned substantially parallel with one another and are generally aligned with the side wall members 120 and 121. In addition to the rear edge support member 134, the apparatus 110 includes a front support member 136 and two side support members 138 and 139. Each side support member measures about 1 inch in width and about 1.25 inches in height. The lengths of the support members are constructed to suitably surround the periphery of the open top edges of the vacuum chamber 112, and are positioned to protrude above the top edges of the chamber wall members by a distance of about 0.5 inch.

A layer of egg crating type material 146 is positioned on top of the support shafts 142 and the top edges of the wall members of the vacuum chamber 112. For example, the egg crating type material can be a translucent light diffuser panel available from McMaster Supply Catalog No. 162 4K 14, having a 13 mm by 13 mm opening in the panel. The egg crating type material extends over a generally rectangular area measuring 23.5 inches by 14 inches, and has a depth measurement of about 0.38 inches. The individual cells of the egg crating structure measure about 0.5 inch square, and the thin sheet material comprising the egg crating is composed of a suitable material, such as polystyrene. A layer of 0.19 mesh nylon screening 148, which measures 23.5 inches by 14 inches, is placed on top of egg crating material 146. Desirably, the mesh nylon screening is a TEFLON-coated, 6 mm mesh nylon screening available from Eagle Supply & Plastic, Inc., Part No. 7308.

A suitable drain line and a drain valve 150 connect to bottom plate member 119 of the vacuum chamber 112 to provide a convenient mechanism for draining liquids from the vacuum chamber 112. The various wall members and support members of tester apparatus 110 may be composed of a suitable noncorroding, moisture-resistant material, such as polycarbonate plastic. The various assembly joints may be affixed by solvent welding, and the finished assembly of the tester is constructed to be watertight. A vacuum gauge 152 operably connects through a conduit into the vacuum chamber 112. A suitable pressure gauge is a Magnahelic differential gauge capable of measuring a vacuum of 0-100 inches of water, such as a No. 2100 gauge available from Dwyer Instrument Incorporated.

The dry product or other absorbent structure is weighed and then placed in an excess amount of 0.9% saline solution and allowed to soak for 20 minutes. After the 20 minute soak time, the absorbent structure is placed on the egg crate material and mesh nylon screening of the Saturated Capacity tester. The latex sheet is placed over the absorbent structure(s) and the entire egg crate grid so that the latex sheet creates a seal when a vacuum is drawn on the tester. A vacuum of 0.5 pounds per square inch (psi) is held in the Saturated Capacity tester for five minutes. The vacuum creates a pressure on the absorbent structure(s), causing drainage of some liquid. After five minutes at 0.5 psi vacuum, the latex sheet is rolled back and the absorbent structure(s) are weighed to generate a wet weight.

The overall capacity of each absorbent structure is determined by subtracting the dry weight of each absorbent from the wet weight of that absorbent determined at this point in the procedure. The 0.5 psi SAT CAP or SAT CAP of the absorbent structure is determined by the following formula:

SAT CAP=(wet weight−dry weight)/dry weight;

wherein the SAT CAP value has units of grams fluid/gram absorbent. For both overall capacity and SAT CAP, a minimum of three specimens of each sample should be tested and the results averaged. If the absorbent structure has low integrity or disintegrates during the soak or transfer procedures, the absorbent structure can be wrapped in a containment material such as paper toweling, for example Hi-Dri® paper towels manufactured by Kimberly-Clark Corporation, Neenah, Wis., U.S.A. The absorbent structure can be tested with the overwrap in place and the capacity of the overwrap can be independently determined and subtracted from the wet weight of the total wrapped absorbent structure to obtain a wet absorbent weight.

Edge Compression Test Method

The method by which the Edge-wise Compression (EC) value Can be determined is set forth below. A 2-inch by 12-inch (5.1 cm by 30.5 cm) piece of the absorbent article including the thickest part of the product is cut with its longer dimension aligned with the longitudinal direction of the product or raw material web. The weight of the sample is determined. The thickness of the material is determined under a 0.2 psi (1.38 KPa) load. The material is formed into a cylinder having a height of 2 inches (5.1 cm), and with the two ends having 0-0.125 inch (0-3.18 mm) overlap, the material is stapled together with three staples. One staple is near the middle of the width of the product, the other two nearer each edge of the width of the material. The longest dimension of the staple is in the circumference of the formed cylinder to minimize the effect of the staples on the testing.

An INSTRON tester, or similar instrument, is configured with a bottom platform, a platen larger than the circumference of the sample to be tested and parallel to the bottom platform, attached to a compression load cell placed in the inverted position. The specimen is placed on the platform, under the platen. The platen is brought into contact with the specimen and compresses the sample at a rate of 25 mm/min. The maximum force obtained in compressing the sample to 50% of its width (1 inch) (2.54 cm) is recorded.

If the material buckles, it is typical for the maximum force to be reached before the sample is compressed to 50%. In a product where the length of the absorbent is less than 12 inches (30.5 cm), the EC value of the material can be determined in the following manner. A detailed discussion of the edge-wise compression strength has been given in *The Handbook Of Physical And Mechanical Testing Of Paper And Paperboard*, Richard E. Mark editor, Dekker 1983 (Vol. 1). Based on theoretical models governing buckling stresses, in the Edge-wise Compression configuration described, the buckling stress is proportional to $E*t^2t/(H^2)$ with the proportionality constant being a function of $H^2/(R*t)$ where E is the Elastic modulus, H is the height of the cylinder, R is the radius of the cylinder, and t is the thickness of the material. Expressing the stress in terms of force per basis weight, it can be shown that the parameter that needs to be maintained constant is $H^2/R$. Therefore, for a sample that is smaller than 12 inches (30.5 cm), the largest possible circle should be constructed and its height (width of the sample being cut out) adjusted such that $H^2/R$ equals 2.1 inches (5.3 cm).

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A pant-like absorbent garment, comprising:
an absorbent chassis defining a waist opening and first and second leg openings, the absorbent chassis including a bodyside liner, an outer cover that defines an exterior surface of the absorbent garment, and an absorbent assembly enveloped in between the bodyside liner and the outer cover, the bodyside liner, the outer cover and the absorbent assembly being integrally assembled together;
the absorbent chassis having a longitudinal length and the waist opening having a circumference, such that the longitudinal length is proportional to the circumference of the waist opening according to the relation:

Length≦(Circumference+128)/1.6, wherein the circumference of the waist opening is measured at 500 grams tension, the garment has a thickness of less than about 4.5 millimeters, and a front elastic waist member and a rear elastic waist member are operatively joined to the outer cover, the body side liner, or both.

2. The garment of claim 1, wherein the garment has a thickness of less than about 3 millimeters.

3. The garment of claim 1, wherein the circumference of the waist opening is between about 450 and about 750 millimeters.

4. The garment of claim 1, wherein the garment has a saturated capacity of between about 100 and about 800 grams.

5. The garment of claim 1, wherein the garment has an edge compression peak load of less than about 1500 grams.

6. A pant-like absorbent garment, comprising:
an absorbent chassis defining a waist opening and first and second leg openings, the absorbent chassis including a bodyside liner, an outer cover that defines an exterior surface of the absorbent garment, and an absorbent assembly enveloped in between the bodyside liner and the outer cover, the bodyside liner, the outer cover and the absorbent assembly being integrally assembled together;
the absorbent chassis having a longitudinal length and the waist opening having a circumference, such that the longitudinal length is proportional to the circumference of the waist opening according to the relation:

Length≦(Circumference+114)/1.6, wherein the circumference of the waist opening is measured at 500 grams tension, the garment has a thickness of less than about 4.5 millimeters, and a front elastic waist member and a rear elastic waist member are operatively joined to the outer cover, the body side liner, or both.

7. The garment of claim 6, wherein the garment has a thickness of less than about 3 millimeters.

8. The garment of claim 6, wherein the circumference of the waist opening is between about 500 and about 700 millimeters.

9. The garment of claim 6, wherein the garment has a saturated capacity of between about 200 and about 500 grams.

10. The garment of claim 6, wherein the garment has an edge compression peak load of less than about 1200 grams.

11. A pant-like absorbent garment, comprising:
an absorbent chassis defining a waist opening and first and second leg openings, the absorbent chassis including a bodyside liner, an outer cover that defines an exterior surface of the absorbent garment, and an absorbent assembly enveloped in between the bodyside liner and the outer cover, the bodyside liner, the outer cover and the absorbent assembly being integrally assembled together;
the absorbent chassis having a longitudinal length and the waist opening having a circumference, such that the longitudinal length is proportional to the circumference of the waist opening according to the relation:

Length≦(Circumference+99)/1.6, wherein the circumference of the waist opening is measured at 500 grams tension, the garment has a thickness of less than about 4.5 millimeters, and a front elastic waist member and a rear elastic waist member are operatively joined to the outer cover, the body side liner, or both.

12. The garment of claim 11, wherein the garment has a thickness of less than about 2 millimeters.

13. The garment of claim 11, wherein the circumference of the waist opening is between about 500 and about 700 millimeters.

14. The garment of claim 11, wherein the garment has a saturated capacity of between about 200 and about 500 grams.

15. The garment of claim 11, wherein the garment has an edge compression peak load of less than about 800 grams.

16. A process for making a pant-like absorbent garment, comprising:
determining a desired waist circumference for the absorbent garment, measured at 500 grams tension;
determining a desired longitudinal length of the absorbent garment from the following equation:

Length≦(Circumference−b)/m; and making an absorbent garment having a longitudinal length determined from the equation, the absorbent garment including an absorbent chassis defining the waist circumference and first and second leg openings, the absorbent chassis including a bodyside liner, an outer cover that defines an exterior surface of the absorbent garment, and an absorbent assembly enveloped in between the bodyside liner and the outer cover, the bodyside liner, the outer cover and the absorbent assembly being integrally assembled together, wherein the garment has a thickness of less than about 4.5 millimeters, and wherein a front elastic waist member and a rear elastic waist member are operatively joined to the outer cover, the body side liner, or both.

17. The process of claim 16, wherein m = 1.6.
18. The process of claim 16, wherein b = −128.
19. The process of claim 16, wherein b = −114.
20. The process of claim 16, wherein b = −99.

* * * * *